United States Patent
Eick et al.

(10) Patent No.: US 7,664,550 B2
(45) Date of Patent: Feb. 16, 2010

(54) METHOD AND APPARATUS FOR DETECTING LEFT VENTRICULAR LEAD DISPLACEMENT BASED UPON EGM CHANGE

(75) Inventors: Olaf J. Eick, Bremen (DE); Koen Michels, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 759 days.

(21) Appl. No.: 10/999,334

(22) Filed: Nov. 30, 2004

(65) Prior Publication Data

US 2006/0116747 A1 Jun. 1, 2006

(51) Int. Cl.
*A61N 1/372* (2006.01)

(52) U.S. Cl. ............... 607/27; 607/28; 607/37
(58) Field of Classification Search .......... 607/27, 607/28, 37; 600/510
See application file for complete search history.

(56) References Cited

U.S. PATENT DOCUMENTS

| | | | |
|---|---|---|---|
| 5,891,179 A * | 4/1999 | Er et al. ................ | 607/27 |
| 5,910,120 A | 6/1999 | Kim et al. | |
| 6,067,469 A * | 5/2000 | Kim et al. ................ | 607/4 |
| 6,195,584 B1 | 2/2001 | Hill et al. | |
| 6,347,249 B1 | 2/2002 | Kim et al. | |
| 6,445,952 B1 | 9/2002 | Manrodt et al. | |
| 6,490,486 B1 * | 12/2002 | Bradley ................ | 607/28 |
| 6,754,531 B1 * | 6/2004 | Kroll et al. ................ | 607/14 |
| 2002/0107553 A1 | 8/2002 | Hill et al. | |
| 2002/0161295 A1 * | 10/2002 | Edwards et al. ............. | 600/420 |
| 2003/0083709 A1 * | 5/2003 | Zhu et al. ................ | 607/27 |
| 2003/0092995 A1 | 5/2003 | Thompson | |
| 2003/0176807 A1 * | 9/2003 | Goetz et al. ............. | 600/547 |
| 2003/0195603 A1 | 10/2003 | Scheiner et al. | |
| 2004/0098056 A1 | 5/2004 | Ding et al. | |
| 2004/0116975 A1 | 6/2004 | Yu et al. | |
| 2004/0172078 A1 | 9/2004 | Chinchoy | |
| 2004/0172079 A1 * | 9/2004 | Chinchoy ................ | 607/17 |

FOREIGN PATENT DOCUMENTS

WO WO 93/20890 10/1993

* cited by examiner

*Primary Examiner*—Carl H Layno
*Assistant Examiner*—Luther G Behringer
(74) *Attorney, Agent, or Firm*—Reed A. Duthler

(57) ABSTRACT

Displacement or migration of a left ventricular lead located within the coronary sinus or coronary veins of the heart is detected by comparing an electrogram (EGM) waveform pattern from the lead with a stored baseline EGM waveform pattern. Based upon the extent of lead migration, if any, a lead displacement may produce an annunciating response. The patient may be alerted, an electrical stimulus applied through the lead may be adjusted to compensate for lead migration, or an alternative electrode on the lead may be used for EGM sensing and pacing.

6 Claims, 12 Drawing Sheets

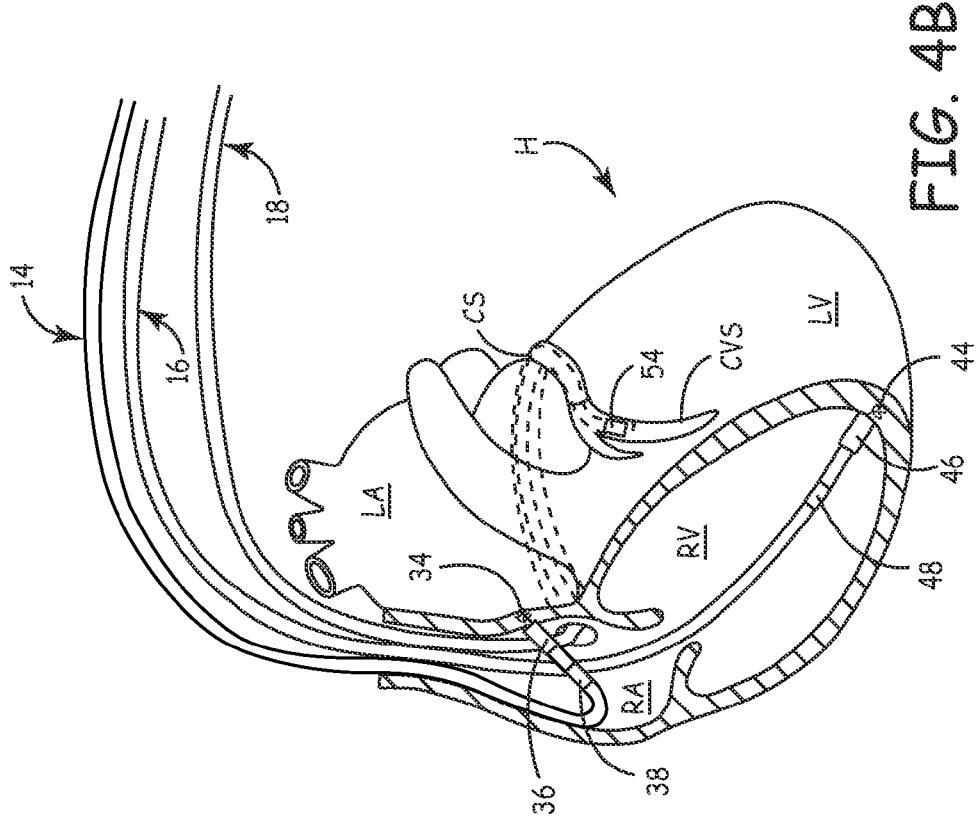
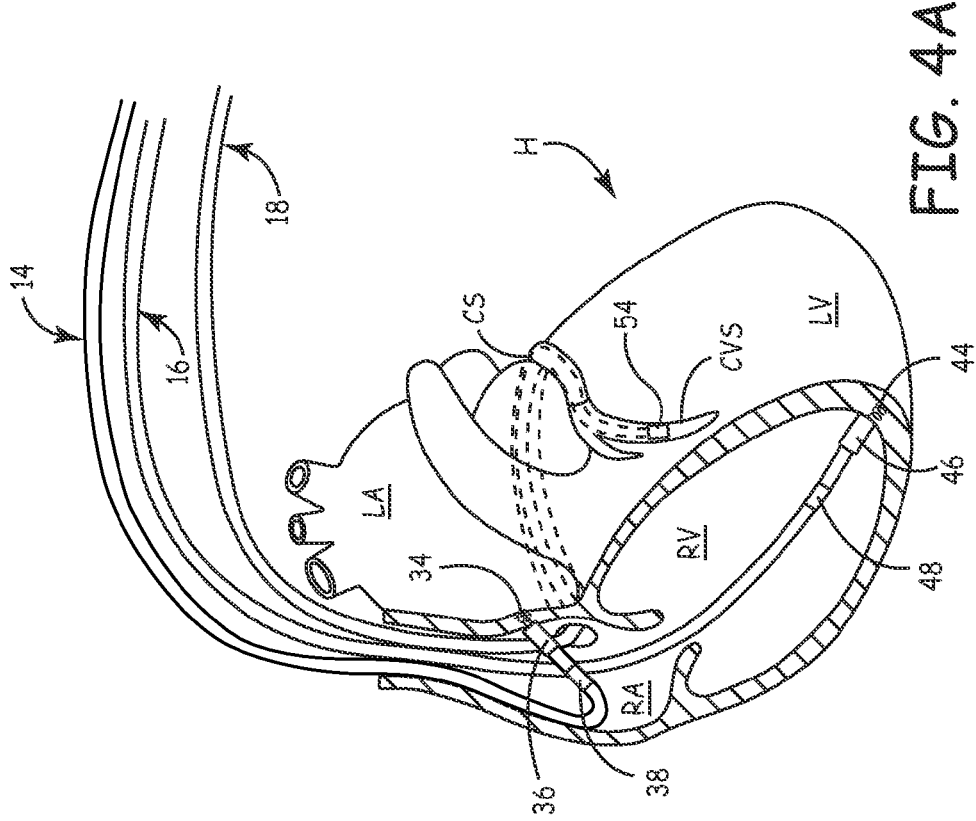

METHOD AND APPARATUS FOR DETECTING LEFT VENTRICULAR LEAD DISPLACEMENT BASED UPON EGM CHANGE

BACKGROUND OF THE INVENTION

The present invention relates generally to cardiac rhythm management systems. In particular, the present invention relates to detection of lead displacement or migration of a sensing/pacing lead, such as a left ventricular lead within the coronary sinus, coronary veins or one or more epicardial or pericardial locations.

In 1957, the first wearable, battery-powered cardiac pacemaker was used to keep a young patient alive. The first implantation of a permanent pacemaker followed in 1958. Since then, pacemaker technology has continually improved and has become the treatment of choice to treat symptoms due to bradycardia. The pacing lead is usually introduced transvenously into the right atrium or right ventricle, and electrical pulses from the implanted pacemaker are applied by the lead via metal electrodes that are in contact with cardiac muscle.

More recently, cardiac resynchronization therapy using bi-ventricular pacing has been introduced to treat patients with heart failure. More than twenty million people worldwide suffer from heart failure, with about two million new cases diagnosed each year. With some patients, heart failure disease affects the synchronous beating action of the left ventricle and right ventricle until the left ventricle cannot pump blood efficiently to supply the body with oxygen and nutrients. These patients tend to tire easily, have a poor quality of life, and their health may deteriorate rapidly resulting in a need of a heart transplant or death.

Cardiac resynchronization therapy helps to coordinate the left ventricle and right ventricle of the heart in patients with moderate to severe heart failure. It helps to improve the pumping power of the heart, can make the patients feel better, increase their energy levels, and improve their exercise capacity.

Cardiac resynchronization therapy systems typically include a left ventricular lead to provide stimulation to the left ventricle, together with conventional pacing leads placed in the right atrium and right ventricle.

The left ventricular lead is oftentimes introduced via the coronary sinus into the coronary venous system to achieve appropriate (synchronous) left ventricular stimulation although a variety of epicardial or pericardial locations can also be utilized. Different patients have different cardiac venous anatomy. As a result, delivery of a left ventricular lead can be challenging. In addition, heart failure can result in cardiac remodeling or change of shape. In contrast to the electrodes of the right atrial pacing lead and the right ventricular pacing lead, which are typically affixed to cardiac muscle by a fixation mechanism such as tines or a screw tip, the electrode (or electrodes) of the left ventricular lead are positioned within a blood vessel and are not affixed by a fixation mechanism. Given the location and the lack of tissue fixation, maintaining the position of the left ventricular lead on a long-term basis can be difficult to achieve. The inventors suggest that in approximately twenty percent (20%) of patients, the left ventricular lead suffers some dislocation, and stimulation may become less effective because the electrode is no longer positioned in the clinically optimal position.

BRIEF SUMMARY OF THE INVENTION

Dislodgement or migration of a lead is detected by comparing an EGM pattern representing heart activity sensed by an electrode of the lead with a previously stored baseline EGM pattern. The baseline pattern represents a characteristic EGM from the electrode of the lead when the electrode was at a position that provided appropriate stimulation.

BRIEF DESCRIPTION OF THE DRAWINGS

FIG. 4A shows a left ventricular lead with an electrode at its implant position.

FIG. 4B shows the left ventricular lead and its electrode at a position after dislodgment or migration of the lead.

DETAILED DESCRIPTION

Figure 1:
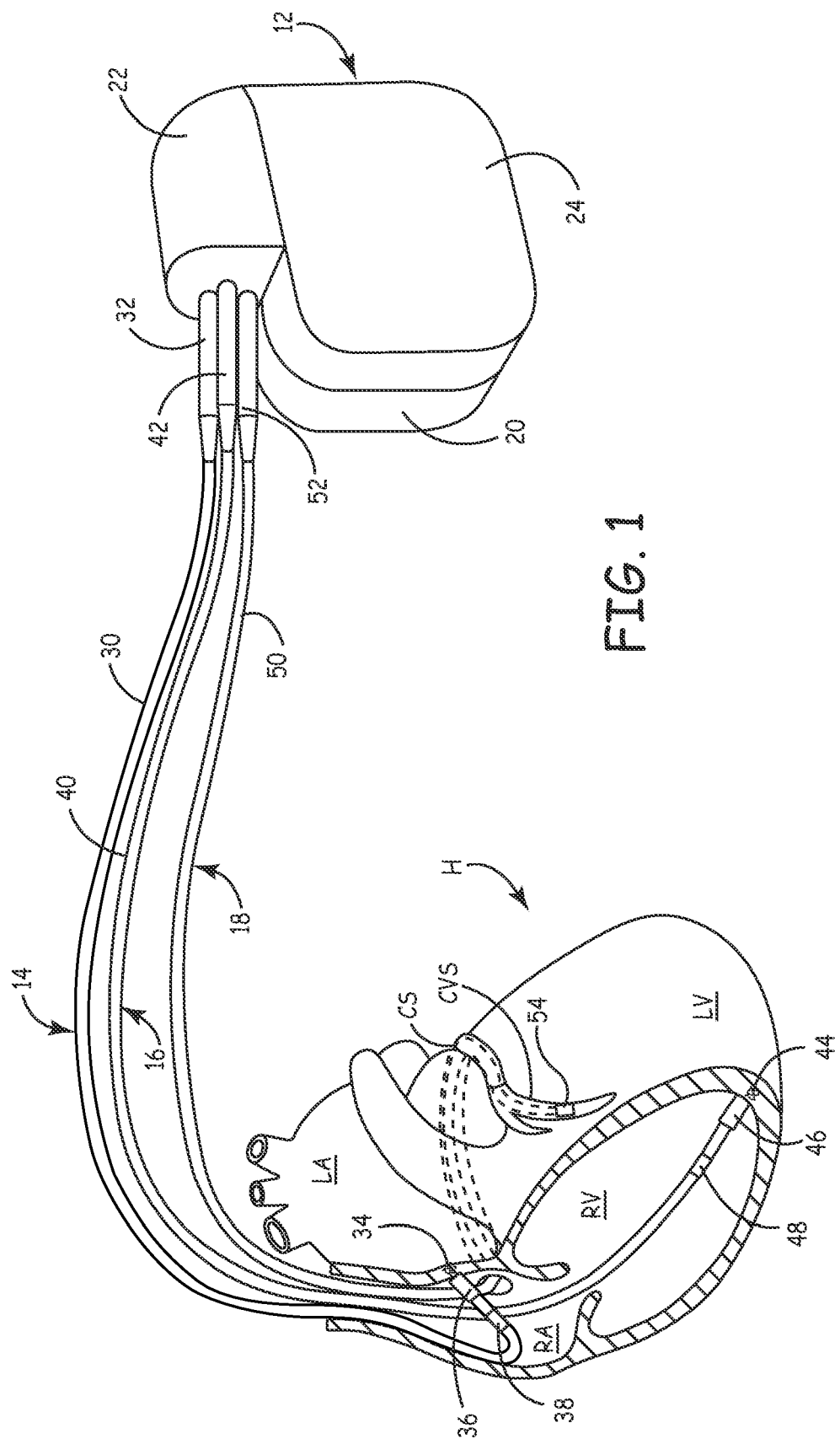
FIG. 1 depicts an example of a cardiac resynchronization therapy (CRT) system in which the present invention may be implemented.

FIG. 1 shows cardiac resynchronization therapy (CRT) system 10, which restores ventricular synchronization in heart H by delivering pacing pulses to one or more chambers of heart H. In FIG. 1, heart H is shown in a partially cutaway view illustrating right atrium RA, left atrium LA, right ventricle RV, left ventricle LV, coronary sinus CS, and coronary venous system CVS.

CRT system 10 includes pacemaker 12, right atrial (RA) lead 14, right ventricular (RV) lead 16, and left ventricular (LV) lead 18. As shown in FIG. 1, pacemaker 12 includes housing or canister 20, header 22 and can electrode 24. The circuitry and power source of pacemaker 12 are located within housing 20. The circuitry communicates with leads 14, 16, and 18 through electrical connectors within header 22. Can electrode 24 is formed on or is a part of the outer surface of housing 20, and acts as a remote indifferent electrode with respect to one or more of the electrodes carried by leads 14, 16, and 18.

As shown in FIG. 1, RA lead 14 is a bipolar endocardial lead that is passed through a vein into right atrium RA of heart H. RA lead 14 includes lead body 30, connector 32, distal tip attachment mechanism 34, distal tip RA pace/sense electrode 36, and proximal ring RA pace/sense electrode 38. Lead body 30 contains a pair of electrically insulated conductors, which extend from connector 32 to pace/sense electrodes 36 and 38. Connector 32 is inserted into a connection bore within header 22 to provide an electrical connection between pace/sense electrodes 36 and 38 and the circuitry within pacemaker housing 20. The distal end of RA lead 14 is attached to the wall of right atrium RA by attachment mechanism 34, which may be, for example, a screw or tined fastener.

RV lead 16 is a bipolar endocardial lead that is passed through right atrium RA and into right ventricle RV. RV lead 16 includes lead body 40, connector 42, distal tip attachment mechanism 44, distal tip RV pace/sense electrode 46, and proximal ring RV pace/sense electrode 48. Lead body 40 of RV lead 16 contains a pair of electrically insulated conductors, which extend from connector 42 to pace/sense electrodes 46 and 48. Connector 42 is at the proximal end of RV lead 16, and is inserted into a connection bore of header 22 to provide an electrical connection between the pacemaker circuitry within housing 20 and pace/sense electrodes 46 and 48. Distal tip electrode 46 is placed in contact with the apex of right ventricle RV and is fixed in place by attachment mechanism 44. LV lead 18 includes lead body 50, connector 52 and LV pace/sense electrode 54. Lead body 50 contains an electrically insulated conductor, which extends from connector 52 at the proximal end of lead 18 to electrode 54 at the distal end of lead 18 (although other unipolar and bi-polar pace/sense vectors can be used). Connector 52 is inserted into a bore within header 22 to provide electrical connection between LV pace/sense electrode 54 and the pacemaker circuitry within housing 20.

In this embodiment, LV lead 18 is passed through right atrium RA into coronary sinus CS and then into a cardiac vein of coronary vein system CVS. LV lead 18 is shown as a unipolar lead, so that sensing of electrogram (EGM) signals and application of pacing pulses through LV pace/sense electrode 54 is performed with respect to one of the other electrodes 24, 36, 38, 46, or 48 of CRT system 10. Alternatively, LV lead 18 can carry more than one electrode and perform as a bipolar lead or a multipolar lead.

LV lead 18 is configured so that LV pace/sense electrode 54 will lodge within a cardiac vein and will remain in position despite having no mechanical attachment mechanism (e.g., embedded into myocardial tissue or a portion of a vessel wall), comparable to attachment mechanism 34 of RA lead 14 or attachment mechanism 44 of RV lead 16. LV pace/sense electrode 54 is positioned within the cardiac vein during implantation to achieve desired synchronous pacing performance.

Experience has shown that pacing leads can dislodge from their implanted position. This is particularly the case with a left ventricular lead placed within the coronary venous system CVS. With the present invention, dislodgement or migration of LV lead 18 is detected by EGM pattern comparison. At the time of implantation, when LV pace/sense electrode 54 is in its desired final position, an EGM waveform is sensed and stored within memory of pacemaker 12. This stored EGM waveform acts as a baseline (paced or sensed) EGM pattern from which periodic comparison can be made.

At time intervals selected by pacemaker 12 (or selected by an external device in communication with pacemaker 12), an algorithm stored in pacemaker logic causes an EGM waveform to be sensed, stored, and then compared with the baseline pattern. The interval can be programmed by the physician, and can produce a beat-to-beat comparison or a comparison after an elapsed time period, such as every minute, every hour, every day, every week, or longer. Although the EGM waveform can be sensed and stored at any time desired, periods of inactivity of the patient (e.g. at night while sleeping) may be advantageous to reduce possible noise in the waveform produced by patient movement. In addition, a comparison of the baseline signal collected in the same manner (e.g., with the patient positioned in a prone or supine manner).

Upon recognition of a change in the current EGM pattern with respect to the baseline pattern indicating dislodgement or migration of LV pace/sense electrode 54, an annunciating response is produced. This response can be a warning sound or other perceptible signal that indicates to the patient that the patient should visit a physician for further investigation of the electrode location. Alternatively, the annunciating response can cause a change in the pacing pulses applied through LV pace/sense electrode 54 to compensate for a position change. In still another embodiment, which will be described in more detail with respect to FIG. 7, the annunciating response can cause pacemaker 12 to switch to a different LV pace/sense electrode that provides an EGM pattern closest to the baseline pattern.

Figure 2:
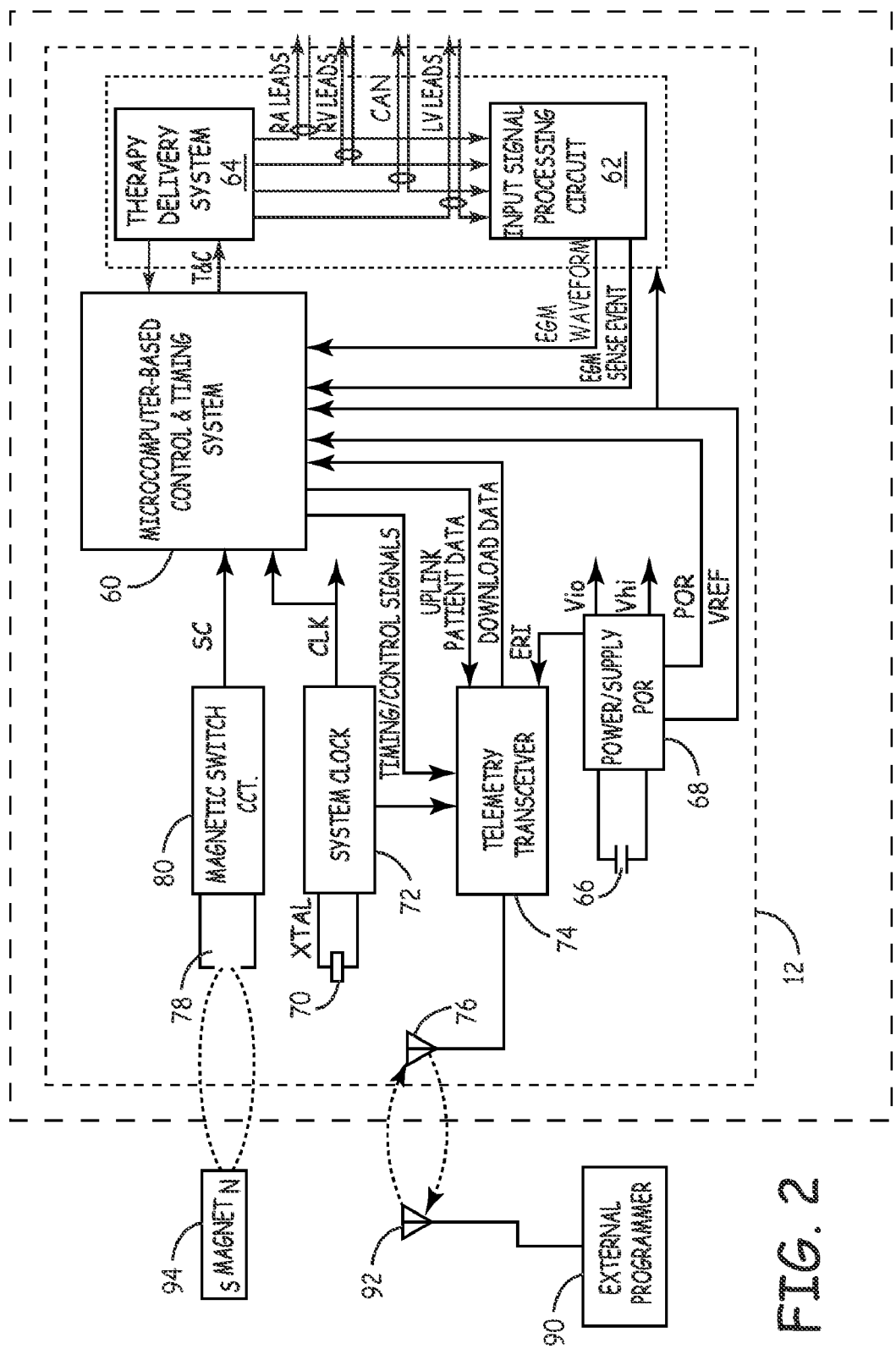
FIG. 2 is a block diagram of an implantable, multi-chamber cardiac pacemaker used in the CRT system of FIG. 1.

FIG. 2 is an electrical block diagram of pacemaker 12 that provides delivery of resynchronization therapy through leads 14, 16 and 18 shown in FIG. 1. As shown in FIG. 2, pacemaker 12 includes microcomputer-based control system 60, input signal processing circuit 62, therapy delivery system 64, battery 66, power supply/power on reset (POR) 68, crystal oscillator 70, system clock 72, telemetry transceiver 74, antenna 76, switch 78, and magnetic switch circuit 80. Also shown in FIG. 2 are external programmer 90 and antenna 92 (which communicate with pacemaker 12 through antenna 76 and transceiver 74), and magnet 94 (which interacts with pacemaker 12 through switch 78 and magnetic switch circuit 80).

Control system 60 controls the functions of pacemaker 12 by executing firmware and program software algorithms stored in associated RAM and ROM. Control system 60 may also include additional circuitry including a watchdog circuit, a DMA controller, a block mover/reader, a CRC calculator, and other specific logic circuitry coupled together by an on-chip data bus, address bus, power, clock, and control signal lines. Control and timing functions can also be accomplished in whole or in part with dedicated circuit hardware or state machine logic rather than a programmed microcomputer.

Input signal processing circuit 62 receives signals from RA lead 14, RV lead 16, LV lead 18 and can electrode 24. The outputs of input signal processing circuit 62 include digitized EGM waveforms and sense event signals derived from the EGM signals sensed by leads 14, 16, and 18.

Input signal processing circuit 62 includes a plurality of channels for sensing and processing cardiac signals from electrodes coupled to leads 14, 16, and 18. Each channel typically includes a sense amplifier circuit for detecting specific cardiac events and an EGM amplifier circuit for providing the EGM waveform signal to control system 60, where the EGM waveform is sampled, digitized and stored.

Therapy delivery system 64 delivers cardiac pacing pulses to leads 14, 16, and 18 to control the patient=s heart rhythm and to resynchronize heart chamber activation. Delivery of the cardiac pacing pulses by therapy delivery system 64 is under the control of control system 60. Delivery of pacing pulses to two or more heart chambers is controlled in part by the selection of programmable pacing intervals, which can include atrial-atriol (A-A), atrial-ventricular (A-V) and ventricular-ventricular (V-V) intervals.

Therapy delivery system 64 can optionally be configured to include circuitry for delivering cardioversion/defibrillation therapy in addition to cardiac pacing pulses for controlling a patient=s heart rhythm. Accordingly, leads 14, 16, and 18 can additionally include high voltage cardioversion or defibrillation shock electrodes.

Electrical energy for pacemaker 12 is supplied from battery 66 through power supply/power on reset (POR) circuit 68. This includes power to operate the circuitry controlling operation of pacemaker 12, as well as electrical stimulation energy for delivery to heart H, and power for telemetry signal transmissions. Power supply/POR circuit 68 provides low voltage power Vlo, power on reset (POR) signal, reference voltage VREF, elective replacement indicator signal ERI and high voltage power Vhi (if pacemaker 12 also has cardioversion/defibrillator capabilities).

Clock signals for operation of the digital logic within pacemaker 12 are provided by crystal oscillator 70 and system clock 72.

Uplink and downlink telemetry capabilities are provided through telemetry transceiver 74 and antenna 76. External programmer 90 can receive stored EGM data, as well as real-time generated physiologic data and nonphysiologic data from control system 60. In addition, programming data can be supplied from external programmer 90 to control system 60.

FIG. 2 also shows magnetic field sensitive switch 78 and magnetic switch circuit 80, which issue a switch closed (SC) signal to control system 60 when magnet 94 is positioned over the subcutaneously implanted pacemaker 12. Magnet 94 may be used by the patient to prompt control system 60 to deliver therapy or to store physiologic data.

Figure 3:
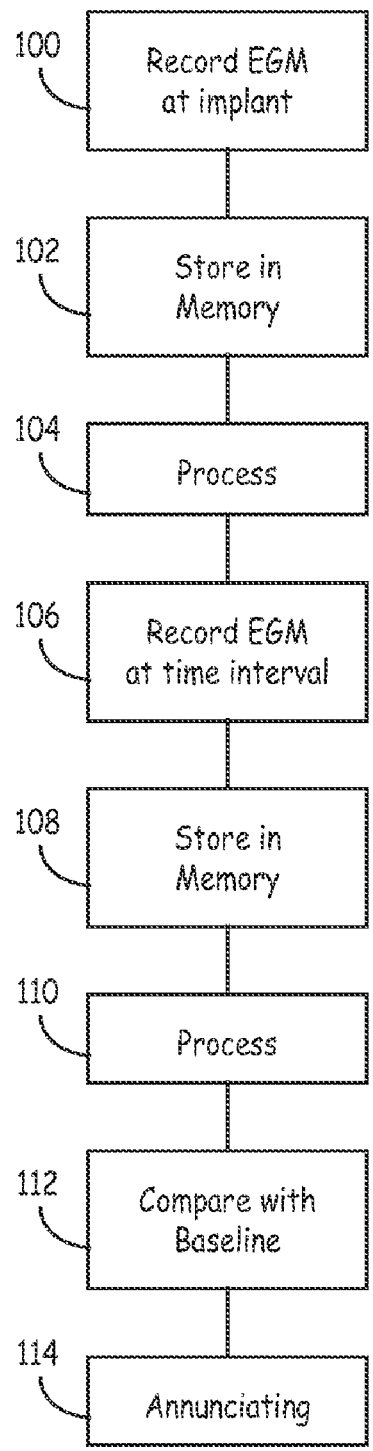
FIG. 3 is a flow chart showing steps performed by the implantable cardiac pacemaker of FIGS. 1 and 2 in accordance of the present invention.

FIG. 3 shows a block diagram of the operation of the present invention. At the time of implant, leads 14,16, and 18 are moved into position. With LV lead 18, LV pace/sense electrode 54 is advanced until appropriate left ventricular stimulation can be achieved. When LV pace/sense electrode 54 is at the proper position, a command is provided from external programmer 90 to control system 60 to record an EGM from LV pace/sense electrode 54. Control system 60 controls input signal processing circuit 62 so that an EGM waveform signal from LV pace/sense electrode 54 is amplified and supplied to control system 60, where it is digitized (step 100) and stored in memory (step 102). The recorded and stored EGM waveform represents a baseline EGM pattern which will be used for later comparison with subsequent EGM patterns derived from LV pace/sense electrode 54. Said baseline EGM pattern can be collected with a patient in one or more of a known, preferably repeatable variety of situations (e.g., different body positions, medicinal regimes, pace/sense electrode configurations, and the like).

At the time of digitizing and storing the EGM waveform baseline pattern, control system 60 may also initiate a transmission of the waveform through telemetry transceiver 74 to external programmer 90, so that the waveform can be reviewed. At the same time, or at a later point in time, the EGM baseline waveform stored in memory is processed by control system 60 (step 104). This waveform processing or analysis can result in derived waveform parameters and characteristics for the EGM baseline pattern which can be used as a basis for comparing the EGM baseline pattern to subsequently generated EGM waveforms. The waveform parameters and characteristics can also be stored for subsequent use, rather than being derived each time a comparison needs to be made.

At a subsequent time, which can be a preset time interval or at a time selected and prompted through programmer 90, control system 60 repeats the process of recording an EGM waveform from LV pace/sense electrode 54 (step 106) and storing the digitized waveform in memory (step 108). The current waveform stored in memory is then processed (step 110) to derive waveform parameters and characteristics. Those parameters and characteristics are then compared (step 112) with similar parameters and characteristics of the baseline EGM pattern. Based upon that comparison, an annunciating response may be generated (step 114).

In some embodiments, multiple EGM waveforms are digitized and stored each time a comparison is to be made. The EGM waveforms can be averaged, or selected ones processed, or each can be processed and compared to the baseline.

Figure 5A:
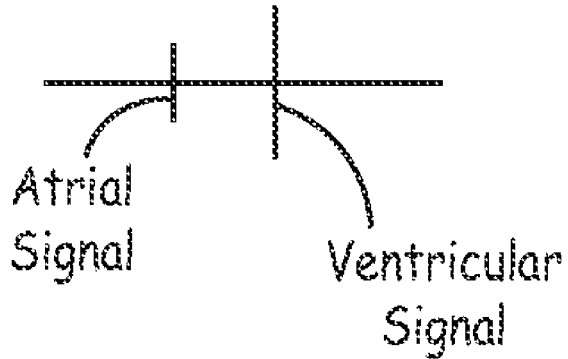
FIG. 5A shows a baseline EGM pattern produced by the electrode at the position shown in FIG. 4A.

FIGS. 4A and 4B and FIGS. 5A and 5B illustrate how the present invention can be used to detect migration or dislodgement of lead 18. In FIG. 4A, LV pace/sense electrode 54 is shown in the same position illustrated in FIG. 1. This is the original or baseline position. FIG. 5A illustrates a baseline EGM pattern derived with LV pace/sense electrode 54 in the position shown in FIG. 4A.

Figure 5B:
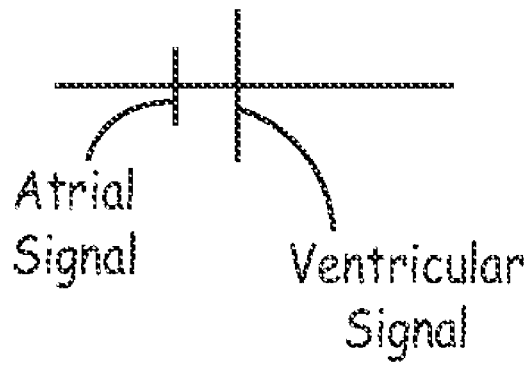
FIG. 5B shows an EGM pattern produced by the electrode at the position shown in FIG. 4B.
Figure 6A:
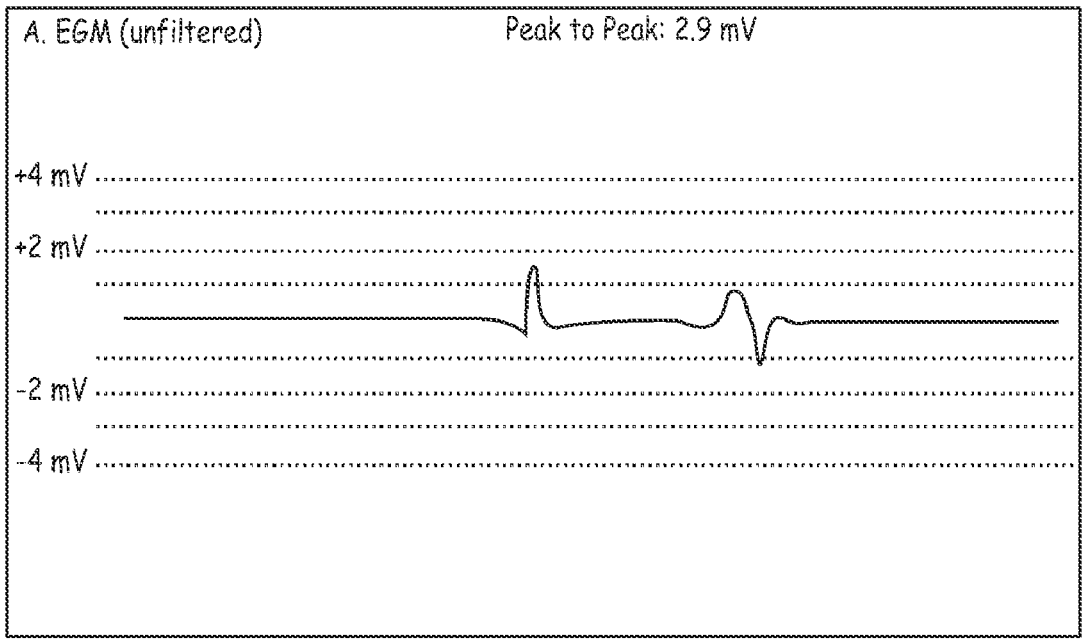
FIGS. 6A-6L show unfiltered bipolar electrogram patterns produced with different electrode positions within the coronary sinus of a goat.
Figure 6B:
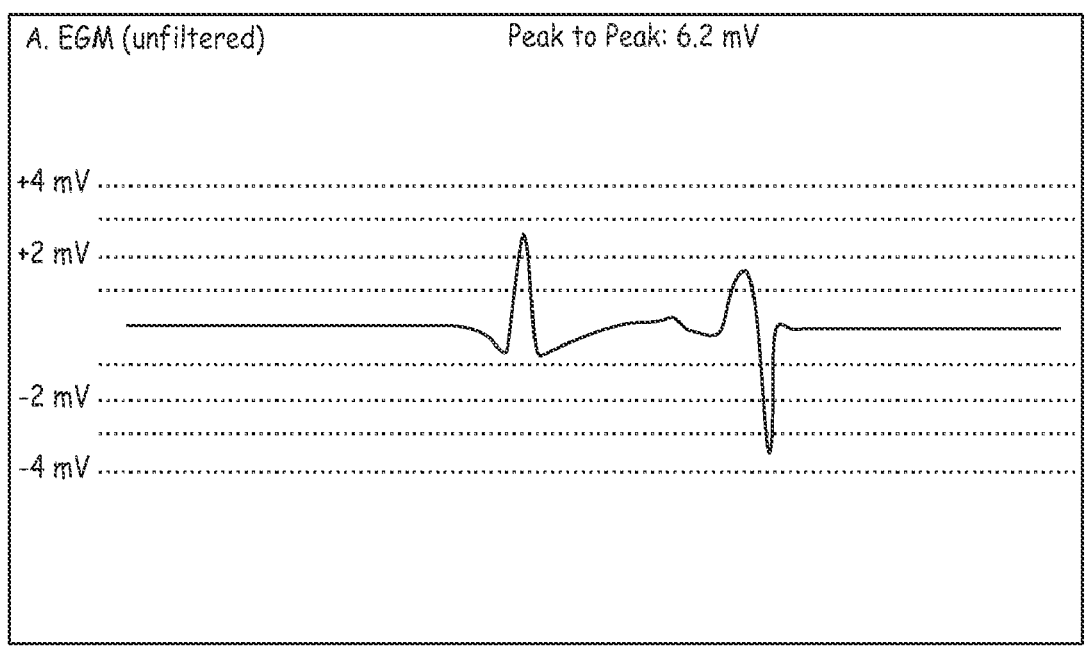
Figure 6C:
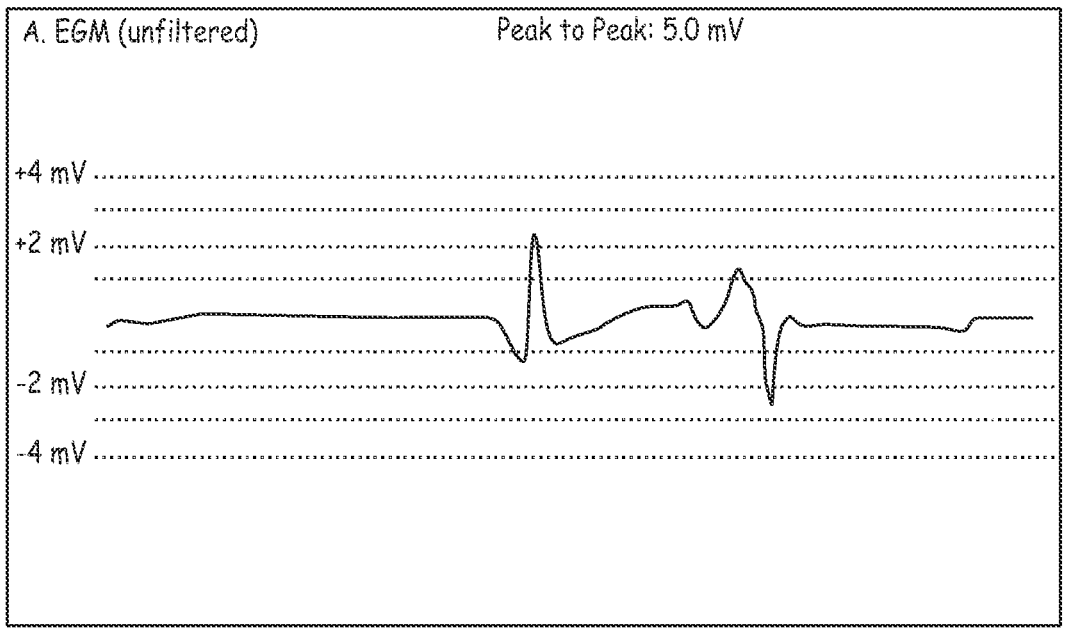
Figure 6D:
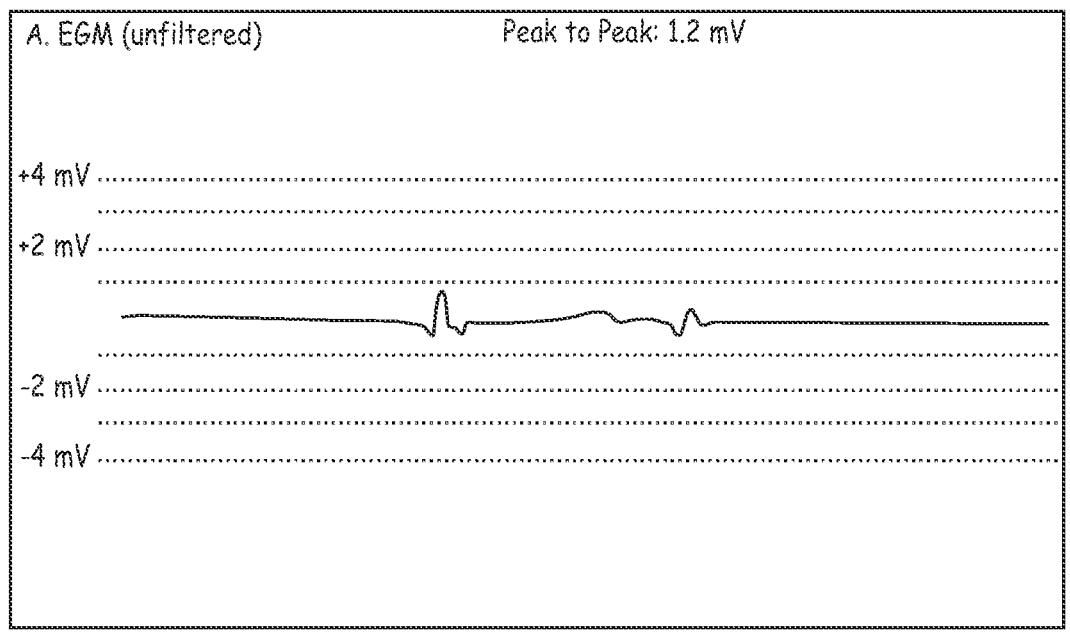
Figure 6E:
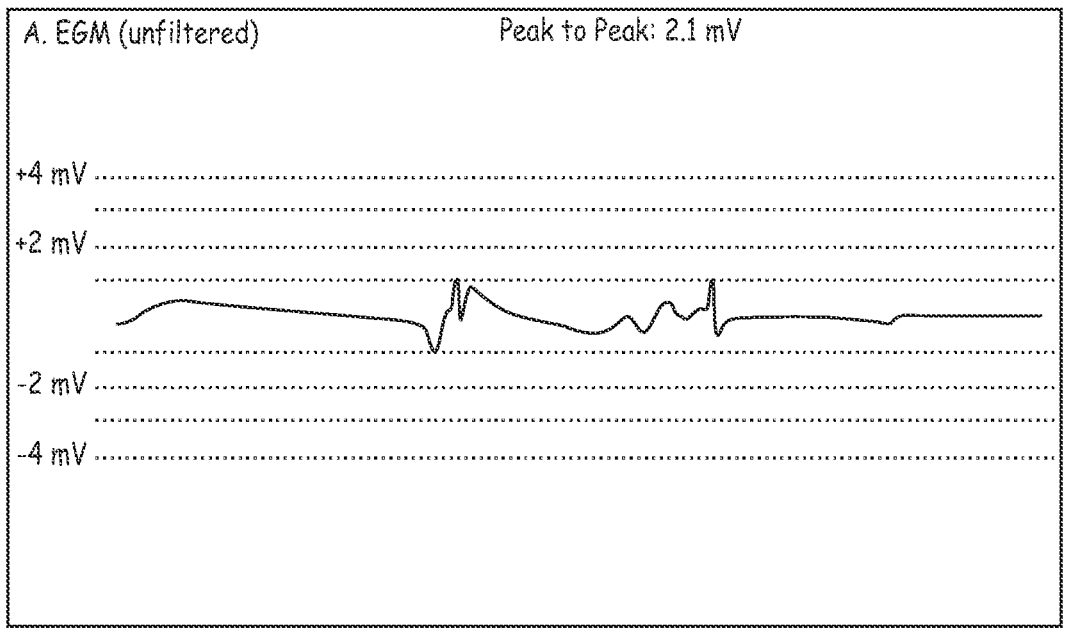
Figure 6F:
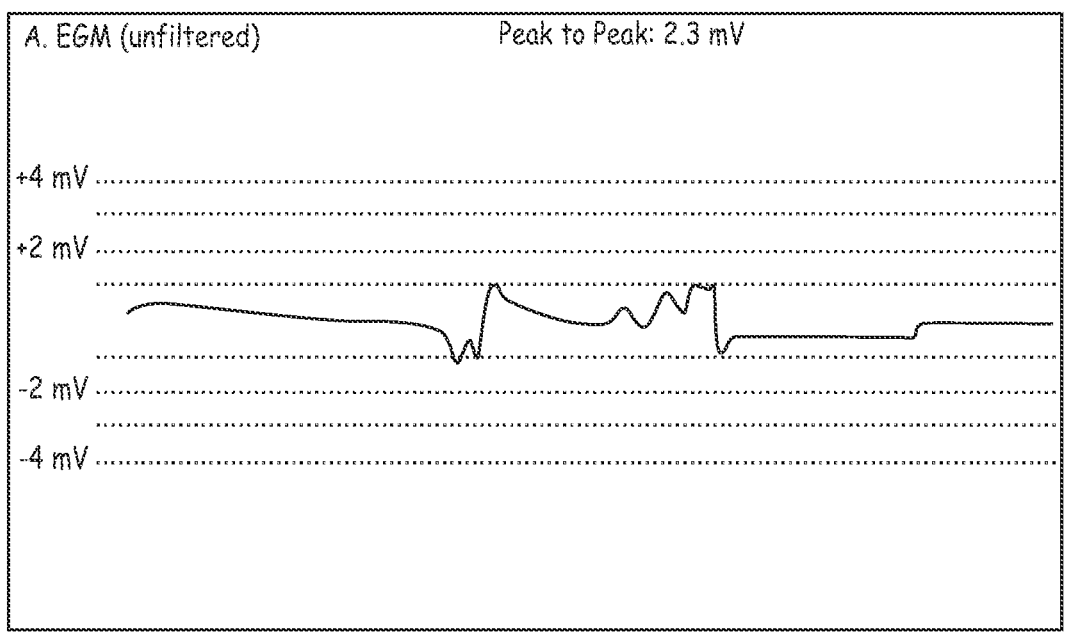
Figure 6G:
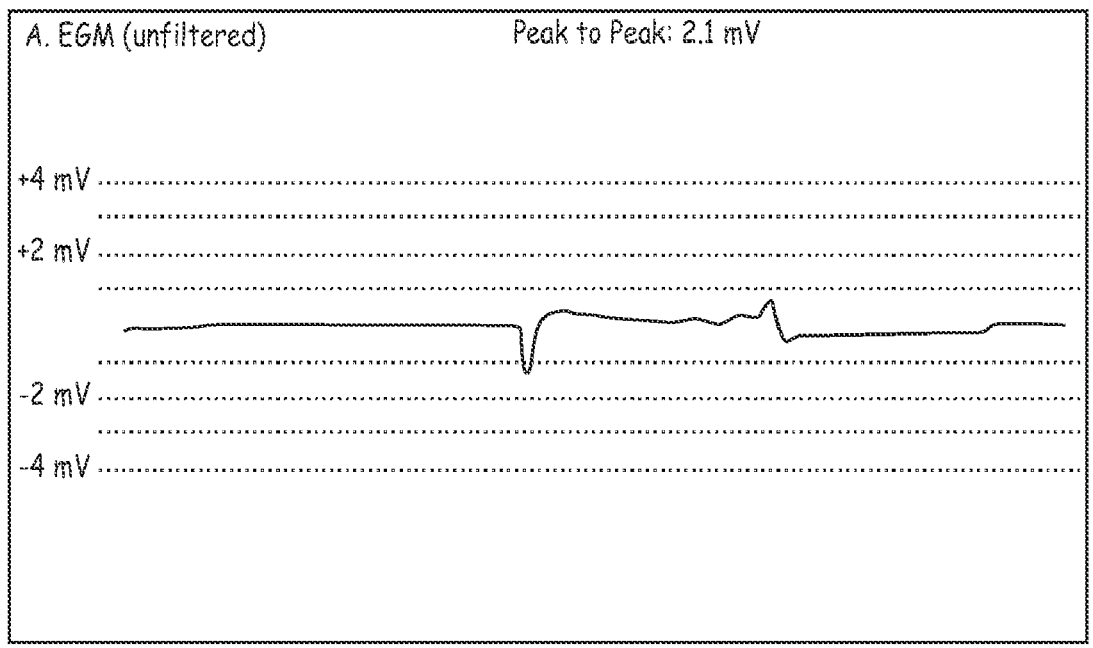
Figure 6H:
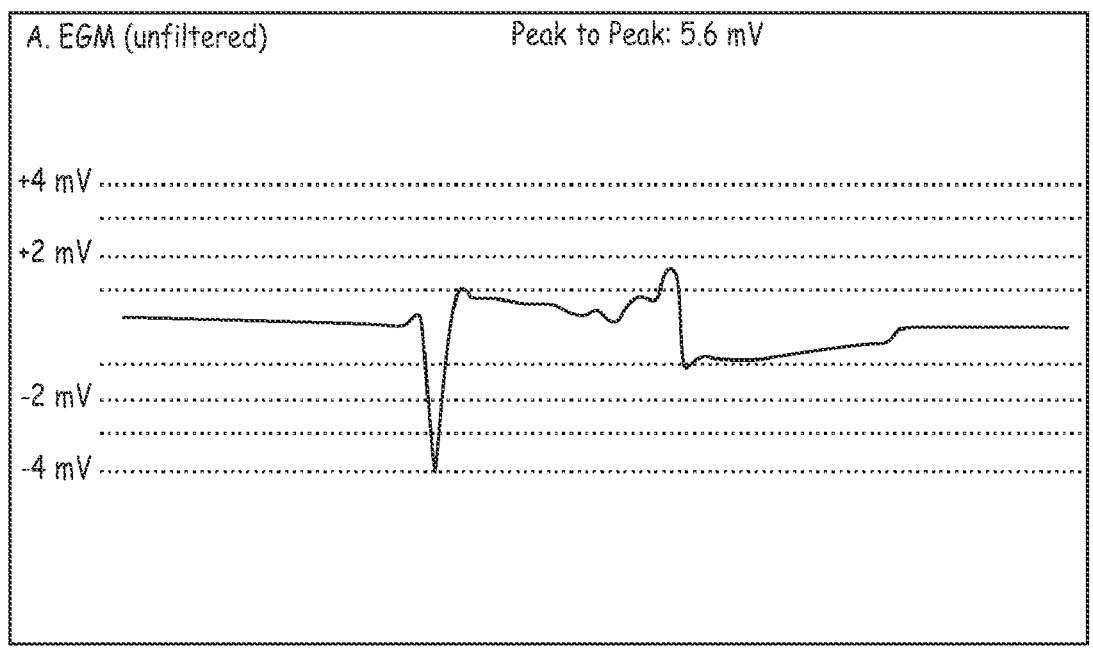
Figure 6I:
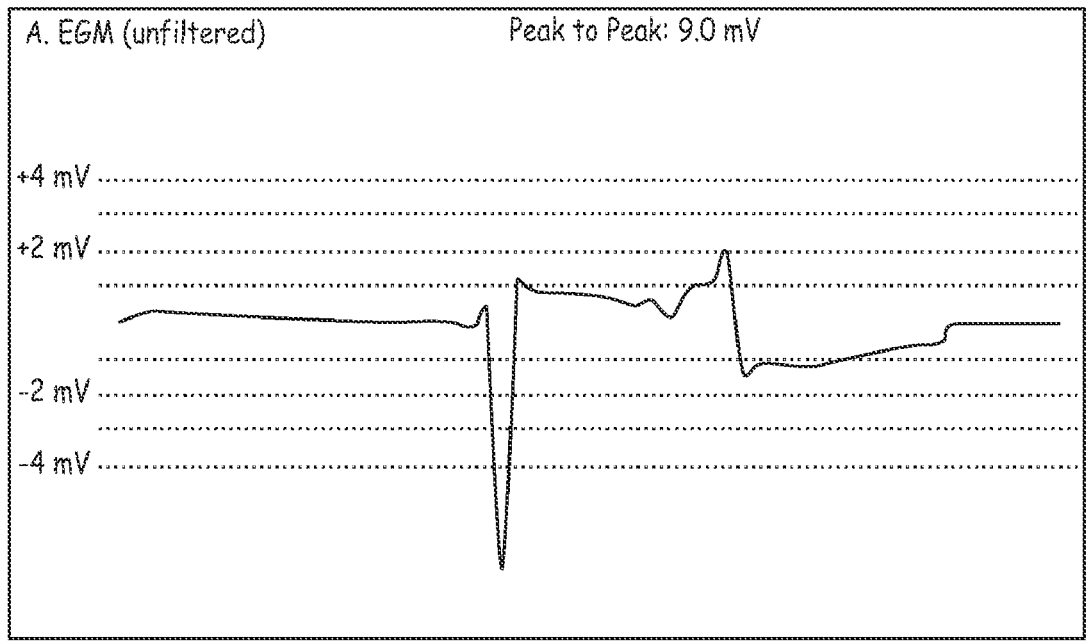
Figure 6J:
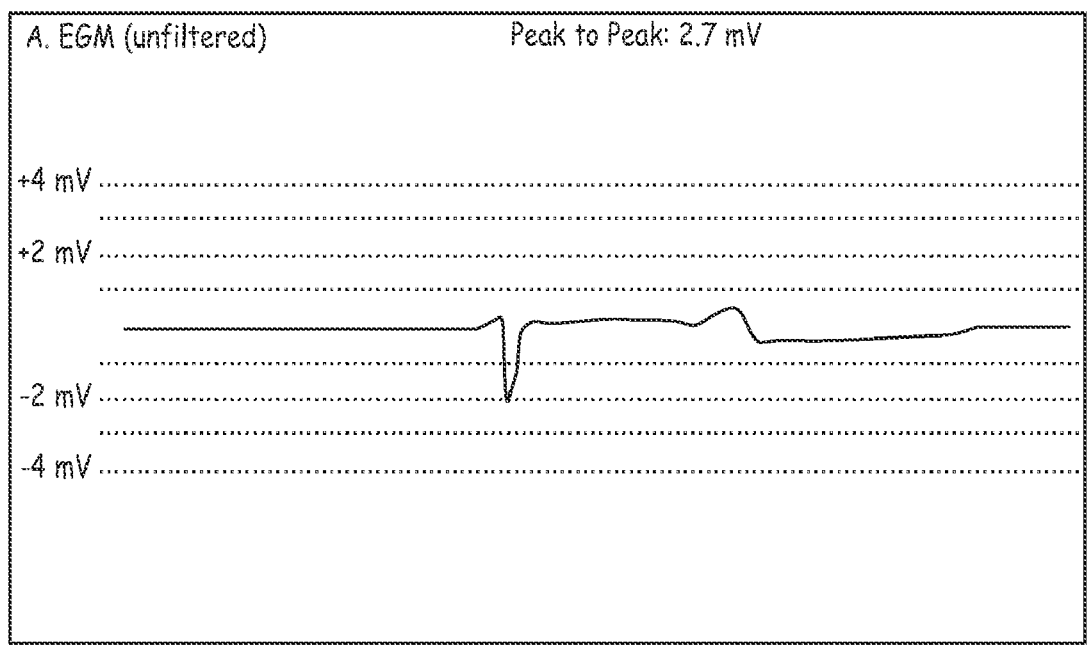
Figure 6K:
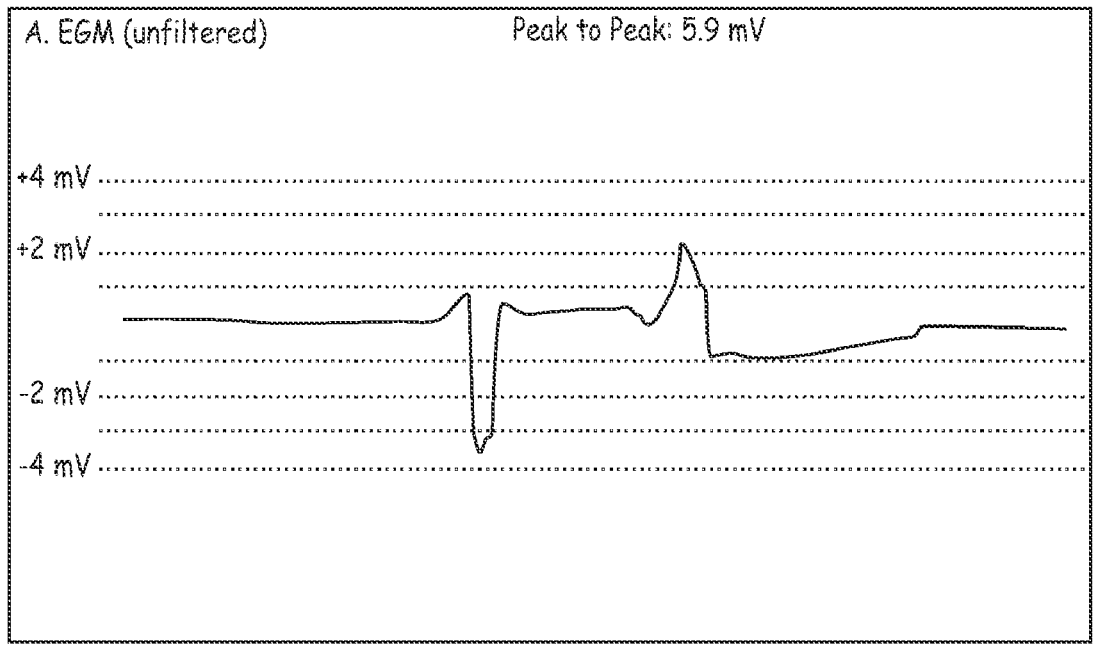
Figure 6L:
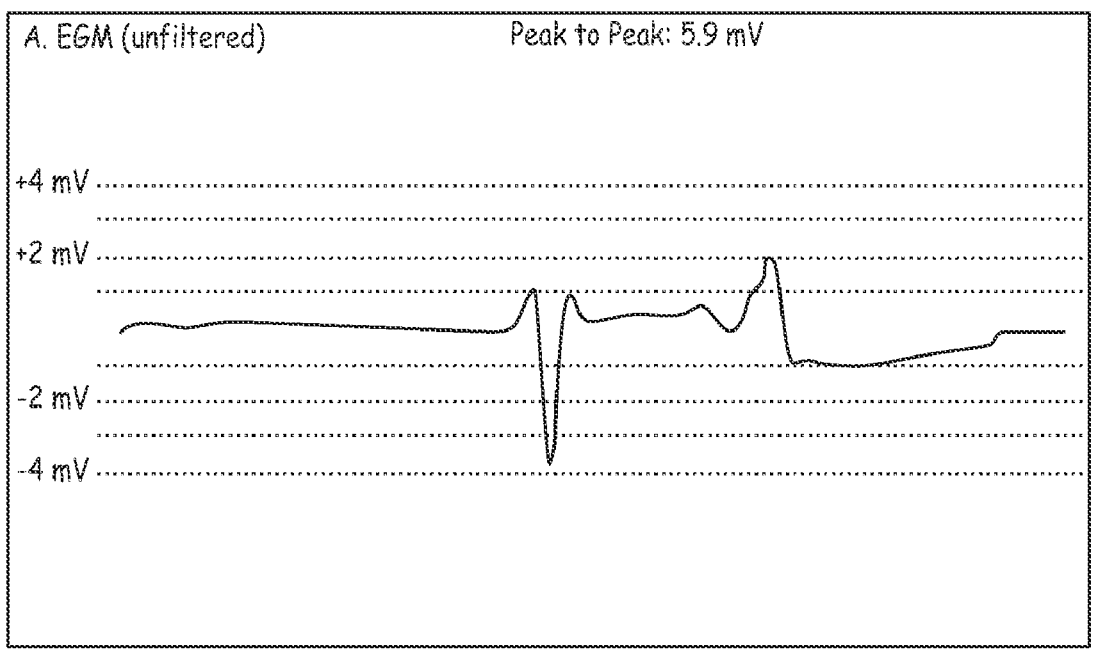

FIG. 4B shows LV lead 18 having been dislocated so that LV pace/sense electrode 54 has migrated away from its original position to a more proximal position. FIG. 5B shows corresponding EGM pattern produced with LV pace/sense electrode 54 in the position shown in FIG. 4B.

FIGS. 5A and 5B show differences in EGM patterns as a result of different lead positions. The changing lead position can result in a change in amplitude, a change in slope (up stroke/downstroke), frequency content, and/or time interval between the atrial and ventricular signals. By comparing waveform characteristics of a baseline EGM pattern and the current EGM pattern, a determination can be made as to whether the position of LV lead 18 (and particularly LV pace/sense electrode 54) has changed sufficiently to warrant an annunciating response.

Although in the example shown in FIGS. 4A, 4B, 5A, and 5B the direction of migration was illustrated as being toward coronary sinus CS, the invention is also applicable to dislodgement or migration in the direction of the coronary veins.

To illustrate the effect of different electrode positions within the coronary sinus and coronary veins, an animal experiment was performed. A lead was positioned in the coronary sinus of a goat, and the position of the electrode carried by the lead was changed within the coronary sinus and coronary venous system to determine whether the resulting EGM waveform pattern would change.

FIGS. 6A-6L represent unfiltered bipolar EGM patterns derived with the electrode at 12 different positions within the coronary sinus/coronary veins. The first spike of each pattern refers to atrial activity, and the second spike to ventricular activity. From FIGS. 6A-6L, it can be seen that amplitude, morphology and timing of the bipolar EGM pattern changes with electrode position. By using multiple parameters or characteristics of the EGM pattern (such as amplitude, shape, waveform, slope, frequency content, and time intervals), change in electrode position can be detected.

Figure 7:
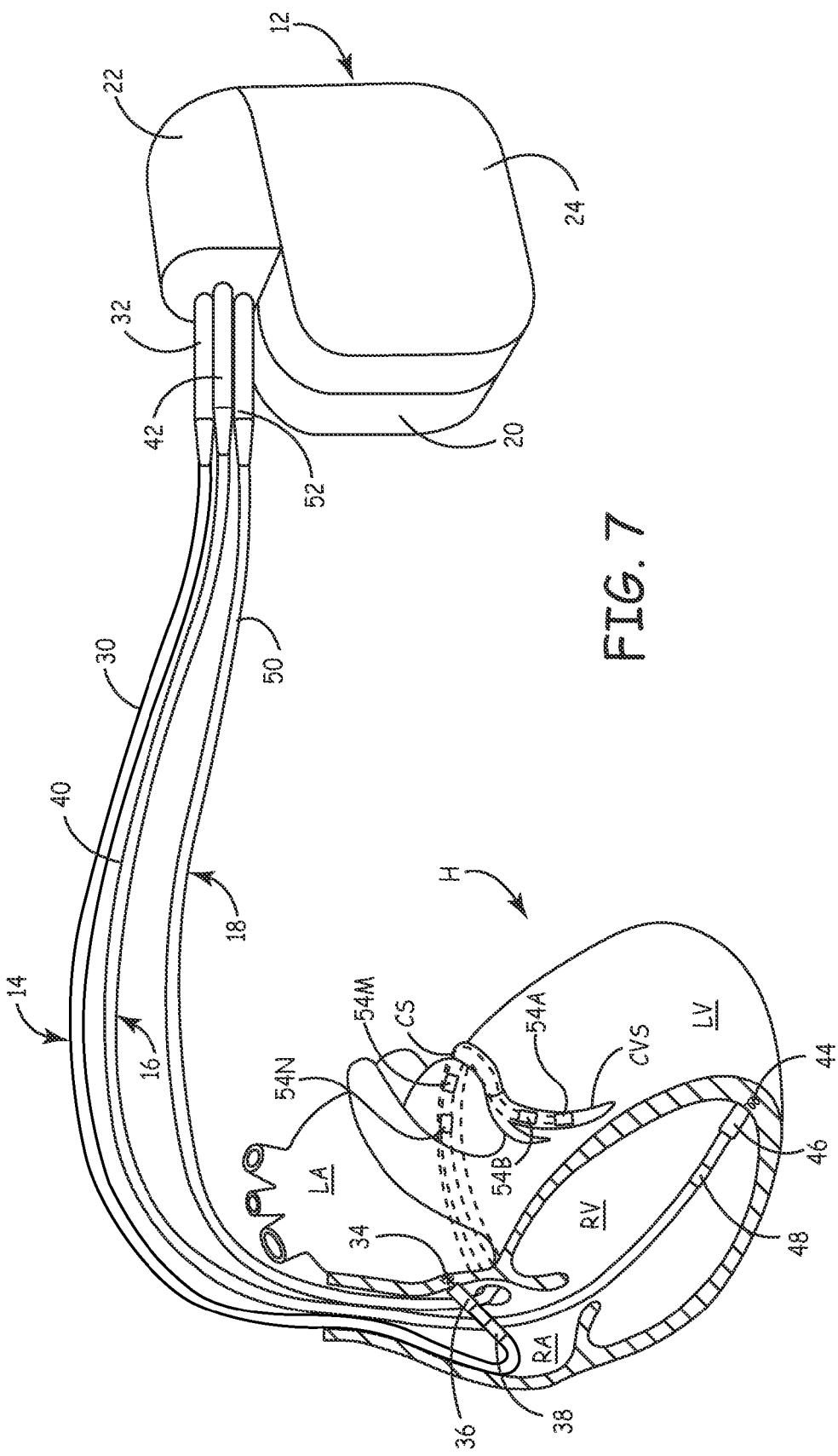
FIG. 7 shows an embodiment of the present invention in which a left ventricular lead includes multiple individually selectable pace/sense electrodes.

FIG. 7 shows another embodiment of the present invention which is generally similar to that illustrated in FIG. 1. The difference, as illustrated in FIG. 7, is that LV lead 18 carries multiple LV electrodes 54A-54N rather than a single electrode (LV pace/sense electrode 54 in FIG. 1). This requires that LV lead 18 contain a separate insulated conductor for each of the LV electrodes 54A-54N.

At the time of implantation, pacemaker 12 of FIG. 7 is instructed to switch from electrode to electrode among LV electrodes 54A-54N, so that the appropriate pacing site can be determined. The LV electrode at that pacing site is then selected for subsequent pacing and sensing. A baseline EGM pattern is derived and stored from the selected LV electrode.

In accordance with the present invention, EGM patterns are derived at a later time for comparison with the baseline pattern. Rather than comparing only one EGM pattern to the baseline, each of the multiple LV electrodes 54A-54N can be considered by comparing the EGM pattern from each LV electrode 54A-54N with the baseline pattern. The LV electrode producing the EGM pattern that is closest to the baseline pattern can then be selected for subsequent pacing and sensing.

The number, size and spacing of LV electrodes 54A-54N depends on the length of possible migration or displacement. A 1 cm movement of LV lead 18 can have a major effect on the therapy delivered. As an example, with a length of 10 cm possible lead movement, ten ring electrodes of 3 mm length and 6 mm to 10 mm spacing can cover that length. Dislodgement tends to be in the direction of the coronary veins, so that a more proximal LV electrode will move into position to provide the therapy.

Although the present invention has been described with reference to preferred embodiments, workers skilled in the art will recognize that changes may be made in form and detail without departing from the spirit and scope of the invention.

The invention claimed is:

1. A method of detecting displacement of an implanted lead having an electrode for pacing and sensing, the method comprising:
    sensing heart activity with the electrode to produce an electrogram (EGM) waveform at time of implantation of the lead;
    storing the EGM waveform sensed at time of implantation as a baseline pattern;
    sensing heart activity with the electrode to produce an EGM waveform at a time subsequent to implantation;
    storing the EGM waveform sensed at the time subsequent to implantation as a subsequent pattern;
    comparing the baseline pattern and the subsequent pattern; and providing an annunciating response as a function of the comparing.

2. The method of claim 1, wherein comparing the baseline pattern and the subsequent pattern comprises:
    processing the baseline pattern to derive a first set of waveform parameters;
    processing the subsequent pattern to derive a second set of waveform parameters; and
    comparing the first and second sets of waveform parameters.

3. The method of claim 1, wherein the annunciating response causes a patient perceptible signal to be produced.

4. The method of claim 1, wherein the annunciating response causes an adjustment in pacing pulse supplied to the electrode.

5. The method of claim 1, wherein the annunciating response causes a different electrode carried by the lead to be used for sensing and pacing.

6. The method of claim 1, wherein the implanted lead comprises one of a left ventricular lead and a lead adapted to be disposed within a portion of the coronary venous system.

* * * * *